(12) United States Patent
Andrei et al.

(10) Patent No.: US 7,282,729 B2
(45) Date of Patent: *Oct. 16, 2007

(54) FABRY-PEROT RESONATOR APPARATUS AND METHOD FOR OBSERVING LOW REFLECTIVITY SURFACES

(75) Inventors: Brunfeld Andrei, Cupertino, CA (US); Gregory Toker, Jerusalem (IL); Clark Bryan, Mountain View, CA (US)

(73) Assignee: Xyratex Technology Limited, Havant, Hampshire (GB)

( * ) Notice: Subject to any disclaimer, the term of this patent is extended or adjusted under 35 U.S.C. 154(b) by 110 days.

This patent is subject to a terminal disclaimer.

(21) Appl. No.: 11/143,018

(22) Filed: Jun. 1, 2005

(65) Prior Publication Data

US 2005/0218350 A1    Oct. 6, 2005

Related U.S. Application Data

(63) Continuation-in-part of application No. 10/644,243, filed on Aug. 20, 2003, now Pat. No. 7,022,978.

(60) Provisional application No. 60/578,192, filed on Jun. 8, 2004.

(51) Int. Cl.
*G01N 21/86* (2006.01)
*G01V 8/00* (2006.01)

(52) U.S. Cl. .................. 250/559.11; 250/216; 356/454

(58) Field of Classification Search ........... 250/559.11, 250/208.1, 235, 216, 227.11, 227.26; 356/28.5, 356/454, 480, 506, 519; 359/337.22, 237–324; 385/8, 9, 18; 355/53, 55, 57; 347/239, 236, 347/246

See application file for complete search history.

(56) References Cited

U.S. PATENT DOCUMENTS 5,225,929 A * 7/1993 Ulanowski .................. 359/389
5,235,192 A   8/1993 Chase et al.

(Continued)

FOREIGN PATENT DOCUMENTS

WO    WO 9416310 A   * 12/1993

OTHER PUBLICATIONS

U.S. Appl. No. 11/149,094, filed Jun. 8, 2005, Toker, et al.

(Continued)

*Primary Examiner*—Georgia Epps
*Assistant Examiner*—Francis M LeGasse, Jr.
(74) *Attorney, Agent, or Firm*—Mitch Harris, Atty at Law, LLC; Andrew M. Harris (57) ABSTRACT

A Fabry-Perot resonator apparatus and method for observing low reflectivity surfaces provides functional improvements for optical inspection and measurement systems, optical storage and retrieval systems as well as other optical systems when the a surface of interest in the resonator path has a lower than ideal reflectivity. The Fabry-Perot resonator is designed with an angle of incidence on the surface of interest deviating from normal incidence, effectively raising the reflectivity. Resonance is supported either by one or more reflectors oriented at angles with respect to the surface of interest, or by a focusing system that alters the directive angle of optical path(s) within the resonator such that the angle of incidence at an intersection of the optical path with the surface of interest is an angle other than normal. A normal incidence is maintained at the reflector(s), so that resonance is supported between the surface of interest and the reflector(s).

22 Claims, 8 Drawing Sheets

U.S. PATENT DOCUMENTS

| | | | |
|---|---|---|---|
| 5,751,427 A * | 5/1998 | de Groot | 356/507 |
| 5,764,365 A * | 6/1998 | Finarov | 356/630 |
| 6,522,471 B2 | 2/2003 | Clark | |
| 6,653,649 B2 | 11/2003 | Clark et al. | |
| 6,700,840 B2 | 3/2004 | Clark | |
| 6,714,295 B2 | 3/2004 | Clark et al. | |
| 6,717,707 B2 | 4/2004 | Clark | |
| 6,778,307 B2 | 8/2004 | Clark | |
| 6,879,421 B2 | 4/2005 | Clark et al. | |
| 6,927,864 B2 | 8/2005 | Clark et al. | |
| 7,022,978 B2 | 4/2006 | Clark et al. | |
| 7,102,740 B2 | 9/2006 | Clark et al. | |
| 2005/0232330 A1 * | 10/2005 | Toker et al. | 372/106 |

OTHER PUBLICATIONS

U.S. Appl. No. 11/169,517, filed Jun. 29, 2005, Brunfeld, et al.
U.S. Appl. No. 11/167,807, filed Jun. 27, 2005, Brunfeld, et al.
U.S. Appl. No. 11/156,309, filed Jun. 17, 2005, Brunfeld, et al.
U.S. Appl. No. 10/770,866, filed Feb. 4, 2004, Brunfeld, et al.

* cited by examiner

FABRY-PEROT RESONATOR APPARATUS AND METHOD FOR OBSERVING LOW REFLECTIVITY SURFACES

CROSS-REFERENCE TO RELATED APPLICATIONS

This application is related to U.S. Provisional Patent Application "Angular Reflectivity Enhancement for Optical Resonators", Ser. No. 60/578,192, filed by the same inventors on Jun. 8, 2004, from which benefit under 35 U.S.C. §119(e) is claimed. The present application is also a Continuation-in-Part of pending U.S. patent application Ser. No. 10/644,243 entitled "METHOD AND APPARATUS INCLUDING IN-RESONATOR IMAGING LENS FOR IMPROVING RESOLUTION OF A RESONATOR-ENHANCED OPTICAL SYSTEM", which was filed on Aug. 20, 2003, now U.S. Pat. No. 7,022,978 having at least one common inventor and assigned to the same assignee, the specification of which is incorporated herein by reference.

BACKGROUND OF THE INVENTION

1. Field of the Invention

This invention relates to optical systems, and more specifically, to an optical system incorporating a resonator to enhance the resolution of optical inspection systems and other optical devices that may include a low reflectivity surface as a surface of interest that lies within a path of resonance reflections in the resonator.

2. Description of the Related Art

Resonator-enhanced optical inspection systems, storage devices and other optical systems, such as those described by U.S. Pat. Nos. 6,653,649, 6,700,840, 6,714,295, 6,717,707, 6,778,307 issued to Applicant Clark and others, the specifications of which are incorporated herein by reference, provide improved resolution, surface detection and other performance improvements in traditional optical systems and provide new types of optical systems that were not available prior to the inventions disclosed therein.

In particular, the combination of a partially reflective surface with a surface under measurement to form a Fabry-Perot resonator provides increased resolution, improved differentiation of surface height and differentiation of surface characteristics, and improved feature detection over the prior available techniques.

However, when forming an optical resonator with a surface having a less than ideal reflectivity at a wavelength or wavelengths at which an optical measurement or detection is either desirable or otherwise dictated, the performance of the resonator is compromised by the reflectivity of the surface.

It would therefore be desirable to improve the performance of the resonator-enhanced optical systems disclosed in the above-referenced patents, as well as other resonator-enhanced optical systems when one of the resonator surface has a less than ideal reflectivity, in order to provide surface measurement or feature detection when the reflectivity of the surface is less than desired.

SUMMARY OF THE INVENTION

The above objective of improving the performance of resonator-based optical systems is achieved in a method and apparatus that increases (away from normal) the angle of incidence of the intra-resonator reflections that impinge on a surface of interest for measurement or detection purposes.

The optical system includes a resonator positioned within a pathway of a measurement beam of the optical system that includes at least one reflector, which includes at least one partially reflective surface. Light leaving the at least one reflector in a normal direction surface is directed at the surface of interest at an angle other than normal and is returned to the at least one reflector along another normal path. The at least one reflector forms part of a resonator that reflects light repeatedly, raising the sensitivity of the optical path to variations and/or features on the surface of interest. One partially reflective surface may act as both plates of the resonator, or a second reflector may be employed with light repeatedly reflected between the reflectors on a path that intersects the surface of interest.

The angular change can be accomplished with two reflectors oriented at the same acute angles with respect to the surface of interest and on opposing sides of the point of intersection of the beam with the surface of interest or by a light-directing device or devices such as a pair of lenses, prisms or a single proximity lens.

The foregoing and other objects, features, and advantages of the invention will be apparent from the following, more particular, description of the preferred embodiment of the invention, as illustrated in the accompanying drawings, wherein like reference numerals indicate like elements.

DETAILED DESCRIPTION OF ILLUSTRATIVE EMBODIMENT

The above-incorporated patent applications describe various resonator-enhanced optical systems, such as optical storage data and retrieval systems having improved data density, optical measurement systems having improved resolution and contrast, and optical systems having improved detector phase/amplitude slope characteristics controlled over portions of the detector response. The above-recited improvements are developed by placement and tuning of resonators within the optical paths of the associated systems.

The present invention concerns a method and resonator apparatus that further improve performance of a resonator-enhanced optical system when a surface of interest forming part of the resonator has less than desirable surface reflectivity at normal incidence of light striking the surface of interest. The improvement is accomplished by altering the resonator so that an angular direction of light striking the surface of interest along a resonant optical path far from normal incidence, thus increasing the reflectivity of the surface of interest and consequently, the finesse of the resonator. In general, if the resonance condition is supported and the reflectivity of each of the involved surfaces is perfect (?=1), then the finesse approaches infinity. However, actual conditions of finite reflectivity due to the reflector material and surface roughness reduce the finesse of the resonator from the ideal condition. By adjusting the angle of incidence at the surface of interest, the effective reflectivity of the surface of interest is improved, increasing the finesse of the resonator. The present invention therefore provides an improvement in all of the above-mentioned resonator-enhanced systems, as well as other systems incorporating Fabry-Perot resonators where improved resonant performance at a particular detection point is desirable on a surface of interest having less than ideal reflectivity.

Figure 1:
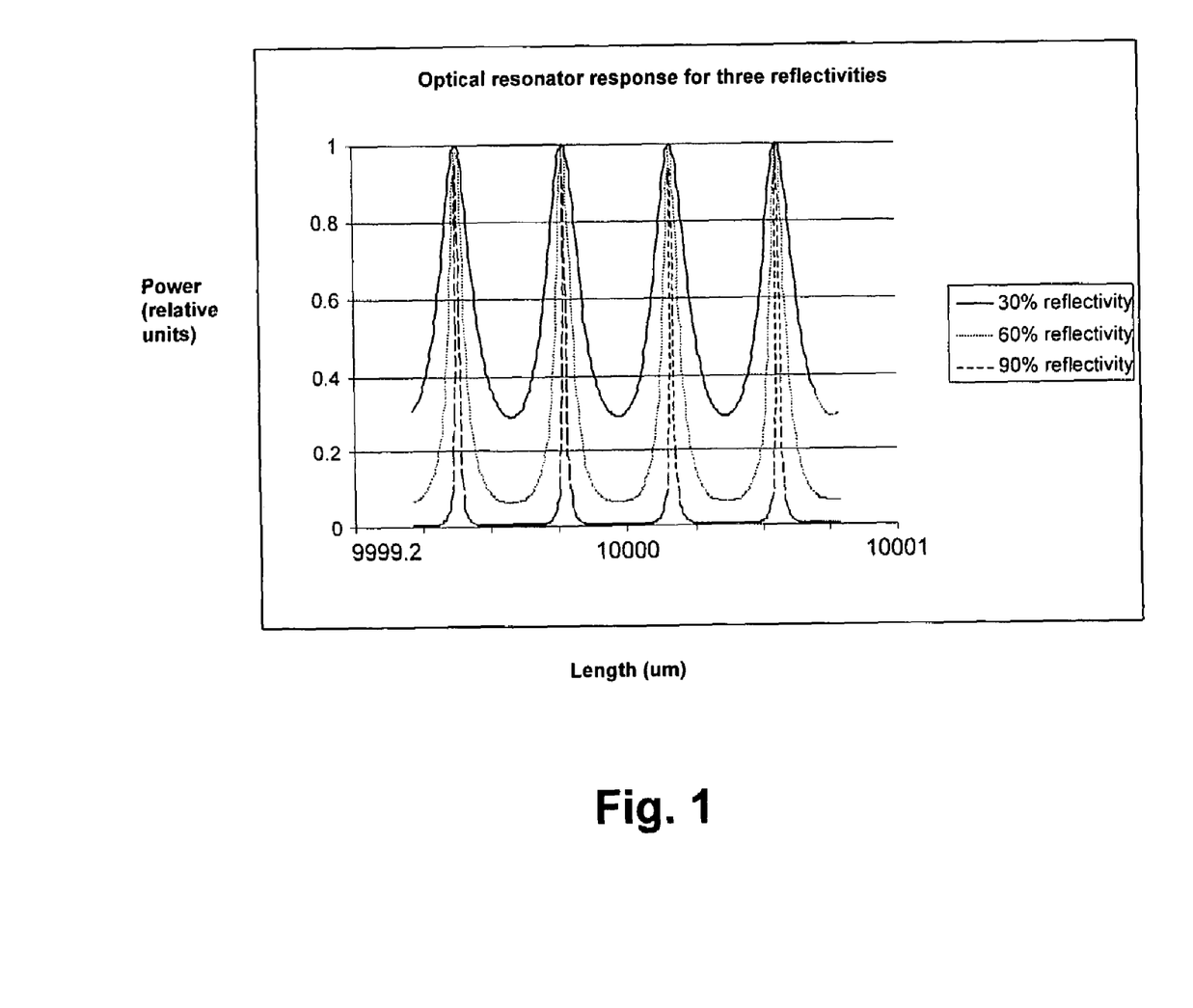
FIG. 1 is a graph showing Fabry-Perot resonator behavior versus surface reflectivity.

Referring to FIG. 1, a graph illustrating the behavior of a Fabry-Perot resonator at three different surface reflectivity levels for a wavelength of 633 nm. The illustrated behavior is a transmission behavior for the resonator, as only at resonance will much energy leave the resonator from the far end. If the resonance is measured from the illumination end of the resonator (i.e., a measurement of the reflected light at the surface of the resonator that is being externally illuminated), then the curve would be inverted and the peaks would be at or near "dark" level, with a high intensity background level away from the resonance peaks.

As can be seen from the illustration, the peaks at 90% reflectivity are much better defined than at lower reflectivity levels, so that when the resonance is used as a detection mechanism, Fabry-Perot resonator with higher reflectivity at the surface of interest provide better discrimination around the resonance points. In a lossless Fabry-Perot resonator, finesse is defined only by the reflectivity of the mirrors. The intensity of the beam transmitted through the Fabry-Perot $$I_T = \frac{BT_1 T_2}{(1-\rho)^2 + 4\rho \sin^2 \frac{\delta}{2}}$$

interferometer $I_T$ is given by:
with $\rho = R_1 R_2 B$ and where $T_1$ and $T_2$ are the transmission of the mirrors, $R_1$ and $R_2$ are the reflectivities of the mirrors, B is the internal transmission of the cavity, and $\delta$ is the accumulated phase on a round trip in the cavity, which is given by $$\delta = 2\frac{2\pi nL}{\lambda}$$

where L is the physical cavity length and n is the refractive index in the cavity.

The contrast of the fringes (the ratio of the maximum to the minimum of the signal) is then given by:

$$C = \left(\frac{1+\rho}{1-\rho}\right)^2$$

and the finesse (the ratio of the distance between the resonance peaks to the peak width) is given by:

$$F = \frac{\pi}{2\sin^{-1}\frac{1-\rho}{2\sqrt{\rho}}} \approx \frac{\pi\sqrt{\rho}}{1-\rho}$$

Losses in the cavity (the fact that ρ<1) occur from transmission, scattering and absorption on the mirrors and also result from any losses in the space(s) between mirrors. In the applications described in the above-incorporated Patent Applications as well as other uses of a Fabry-Perot, the losses on the reference mirror and inside the cavity are usually designed to be minimal. However, when the surface-of-interest (e.g., a surface being measured) is one of the cavity mirrors, then the losses on the surface of interest itself must be taken into consideration. For a geometrically ideal measured surface, the main loss factor is related to the absorption or transmission of the surface. Considering only the influence of the reflectivity of the measured surface, the effective reflectivity ? of the cavity is given by:

$$\rho_{effective} = R_0 \cdot R_2$$

where $R_0$ includes both the first mirror reflectivity $R_1$ and the transmission in the cavity B.

The higher the effective reflectivity ρ, the better the finesse of the resonator, and the better the sensitivity of the any measurement made with the resulting resonator. The sensitivity of a Fabry-Perot interferometer to surface structures is also highly dependent on the length of the cavity and the reflectivity of the tested surface for the specific wavelength and geometry, as is demonstrated by the finesse differences shown in FIG. 1.

Figure 2:
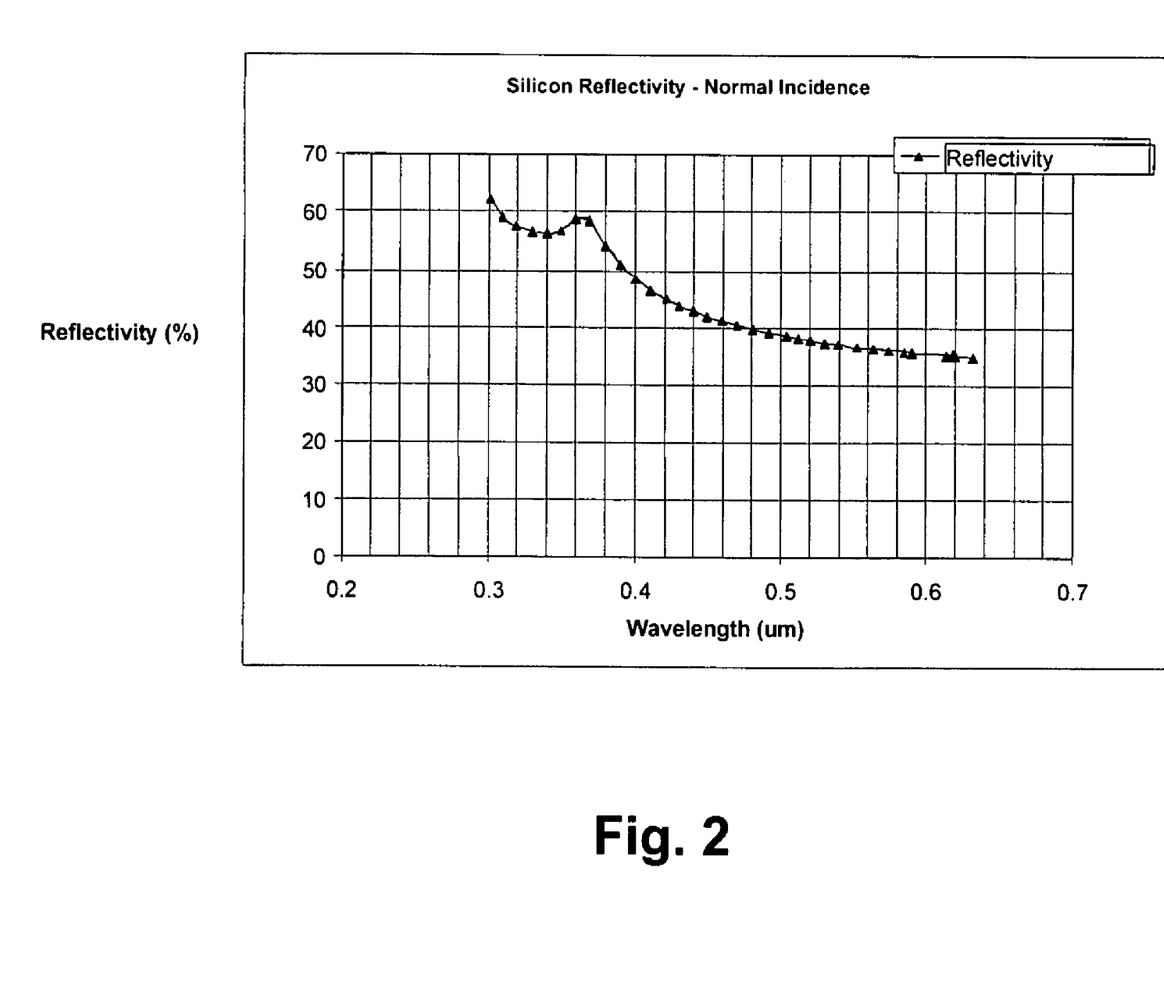
FIG. 2 is a graph showing surface reflectivity of silicon versus optical wavelength.

The reflectivity of a surface is related to its material, which includes its complex refractive index for a specific illumination wavelength, which includes the absorption and transmission characteristics at that wavelength. However, the reflectivity is also a function of the angle of incidence and polarization characteristics of the incident light. When a Fabry-Perot interferometer is adjusted to form an optical resonator, the illumination direction is typically oriented along a direction normal to the two mirrors. Therefore the incidence angle in general is normal and polarization does not affect the reflectivity. The only factor influencing the reflectivity remains the (complex) refractive index. However, if the surface of interest forming part of the resonator presents a low reflectivity at the illumination wavelength, the sensitivity of the optical resonator is affected. A good example of such a material is pure silicon: the reflectivity of pure silicon across a wide spectrum is too low to be considered for resonator measurements. FIG. 2 illustrates the spectral reflectivity response of pure silicon, which is a good approximation for measurements conducted on semiconductor dies and wafers. The reflectivity depicted ranges from just over 60% to just over 30%, a figure too low to provide well-defined resonance peaks as shown in FIG. 1.

Figure 3:
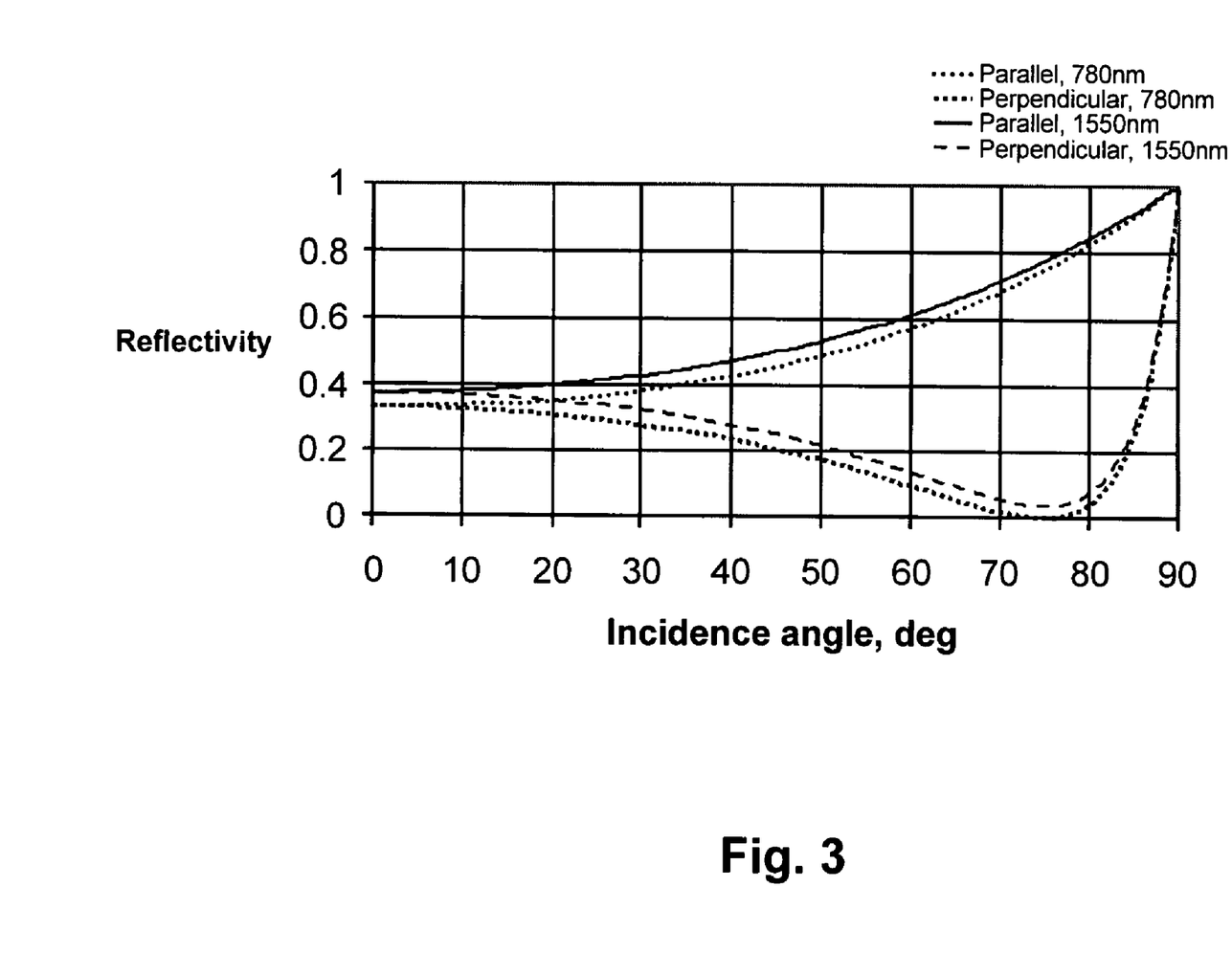
FIG. 3 is a graph showing surface reflectivity of silicon versus angle of incidence.

Referring now to FIG. 3, the effect of incidence angle on the effective reflectivity of pure silicon is depicted at two wavelengths: 780 nm and 1550 nm. At near grazing incidence, both wavelengths show a reflectivity approaching unity, as is expected. Note that for the parallel polarization case, the sensitivity to incidence angle is much higher than for perpendicular polarization, indicating that an angle of incidence as close to grazing as possible would be desirable for Fabry-Perot measurements of silicon device features. In the Brewster region or at the Brewster angle, the reflectivity approaches zero, in this case in the angular region near 75 degrees. Therefore, it would be desirable to make measurements with perpendicular polarization when information about absorption/transmission is not needed. When such information is needed, measurements with both perpendicular and parallel polarizations would be desirable. When measuring with parallel polarization, as can be seen from FIG. 3, measurements must generally be taken at a grazing incidence of less than 5 degrees. If measurements near grazing incidence are not possible and the only other requirement is high reflectivity (such as in the resonator measurements), then measurements around normal incidence would serve better than measurements at a more acute angle.

Figure 4:
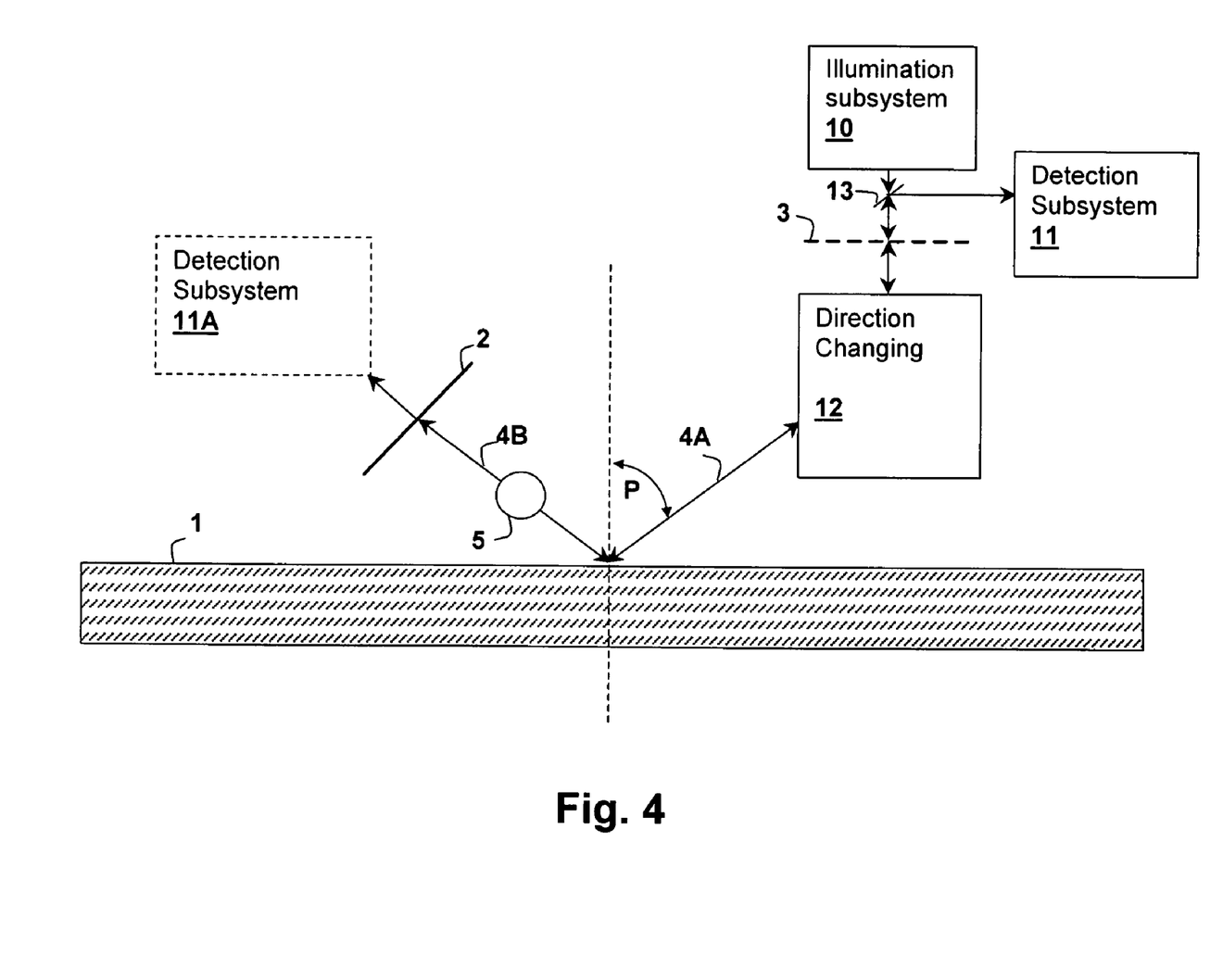
FIG. 4 is a pictorial diagram depicting a triple-reflector optical system in accordance with an embodiment of the invention.

With reference now to FIGS. 4-7D, and particularly to FIG. 4, an optical schematic of a resonator-enhanced optical system in accordance with an embodiment of the invention is illustrated. Resonance is supported between a mirror 2 and a partially reflective surface 3, with surface of interest 1 forming part of the resonance path and intersected by an incident ray 4A and a reflected ray 4B that when combined form a path of resonant length between partially reflective surface 3 and mirror 2. The illustrated system is an example of a three-reflector system that includes surface of interest 1 on a path between two reflectors, namely partially reflective surface 3 and mirror 2. The illustration is purposely generic in that differing types of elements are shown for completeness. However, mirror 2 may also be a partially reflective surface, and although detection subsystem 11 and illumination subsystem 10 are shown at one end of the resonant path, if mirror 2 is replaced with a partially reflective surface, detection subsystem 11 can be located beyond the partially reflective surface (mirror) 2, as illustrated by alternate detection subsystem 11A. If illumination subsystem 10 and detection subsystem 11 are co-located as shown, then a coupler/splitter 13 is included (generally another partially reflective surface oriented at an angle) to couple light to detection subsystem 11 while permitting an illumination beam to pass from illumination subsystem 10 through to partially reflective surface 3.

It should be noted that the Fabry-Perot fringes of the two detection schemes illustrated are complementary. While alternate detection subsystem 11A provides "zero" background and a high output level for positive transmission resonances, detection subsystem 11 yields a high background level, with resonances peaking toward a "zero" level, as mentioned above with respect to the resonances illustrated in FIG. 1.

Within the resonator formed by mirror 2 and partially reflective surface 3 various elements may be introduced and one is required if partially reflective surface 3 is oriented as shown: a direction changing element 12. Direction changing element may be one of many specific elements as will be described in further detail below, but the basic function performed by direction changing element 12 is to shift the direction of the light leaving partially reflective surface 3 to an angle P away from normal, so that the angle of incidence of incident ray 4A is far from normal at the intersection of ray 4A with surface of interest 1. An alternative to including direction changing element 12 is to orient partially reflective surface 3 at an angle complementing that of mirror 2 so an incident ray 4A leaving partially reflective surface 3 in a normal direction strikes surface of interest at an angle other than normal.

Another feature that may be included in the optical system is the inclusion of one or more focusing elements 5 within the resonant path. As depicted, focusing element 5 is included in the reflected path illustrated by ray 4B, and is used as a "cat's eye" retro-reflector to image surface of interest 1 onto mirror 2, which reduces the sensitivity of the system to the angular position of surface of interest 1 (or surface features causing an inclination) that would reduce the optical resonance in the system.

If included in illumination path 4A, an alternative focusing lens 5 provides for better spatial resolution at surface of interest 1, providing better interaction between the illuminating optical field passing through partially reflective surface 3 and arriving at surface of interest 1. In general, it is desirable to include focusing elements on both the illumination and detection optical paths, in order to increase the sensitivity of the system to changes in surface of interest 1, while decreasing the sensitivity of the system to angular errors between surface of interest 1 and reflectors 2,3.

Focusing elements 5 included within the system can be adjusted for imaging with an infinite conjugation ratio (i.e., to collimate the beams) or with finite conjugation ratio (i.e., to focus such that reflectors 2,3 are imaged onto surface of interest 1.

Figure 5:
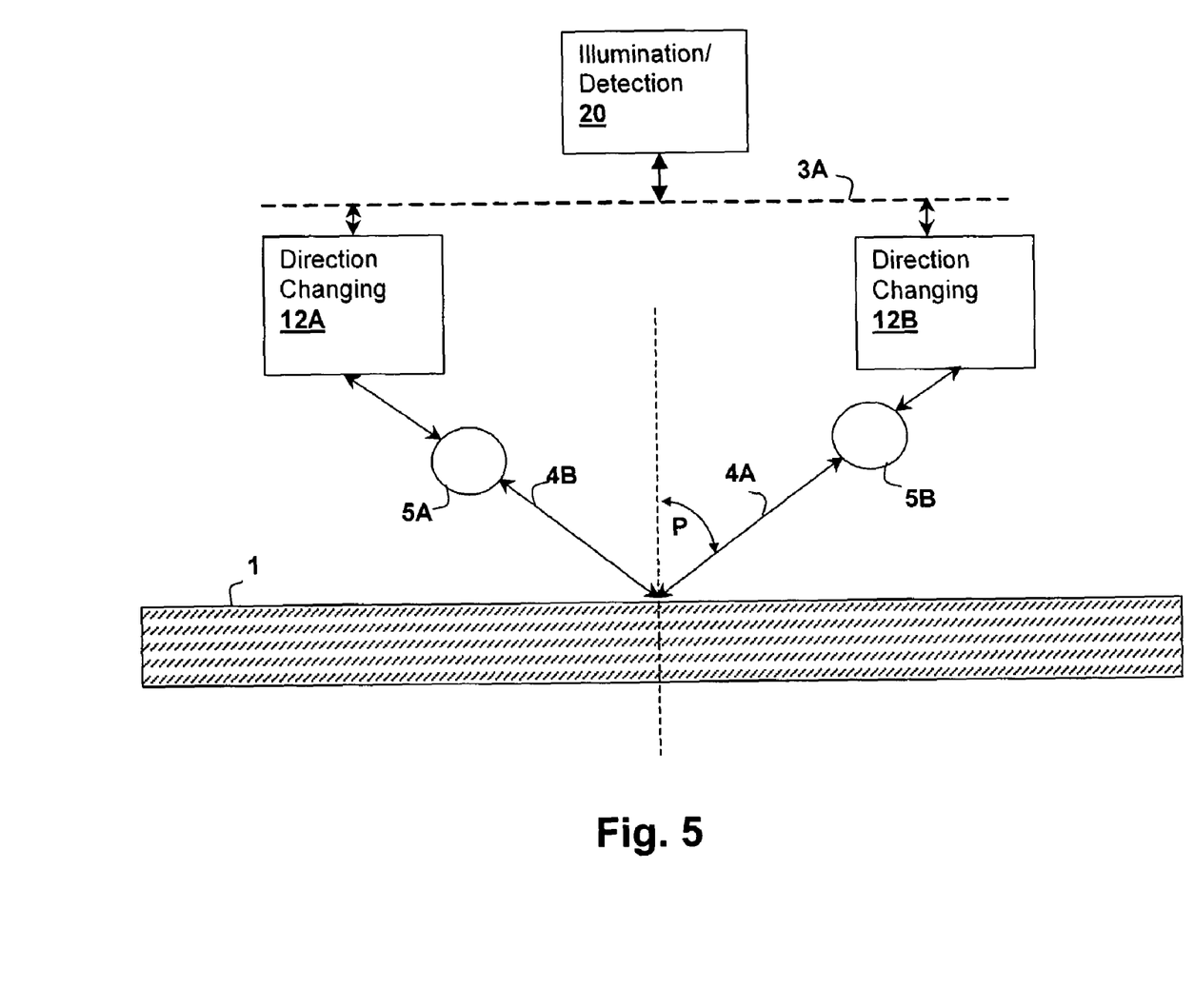
FIG. 5 is a pictorial diagram depicting a dual-reflector optical system in accordance with another embodiment of the invention.

Referring now to FIG. 5, a dual-reflector Fabry-Perot measurement system in accordance with another embodiment of the invention is shown. The dual-reflector system is less complicated than the triple mirror system described above, but is less flexible with respect to configuration. In the depicted embodiment, one partially reflective surface 3A provides a first reflector and surface of interest 1 provides the other reflector. However, the resonant path terminates only on partially reflective surface 3A at two distinct locations for each ray, with surface of interest 1 as an intermediate point on the path. The above is accomplished by incorporating two direction changing elements 12A and 12B that may be formed as a single element that has a direction-changing characteristic on either side of the point of intersection of rays 4A and 4B with surface of interest 1. Direction changing elements 12A and 12B alter the angular direction of light leaving and striking partially reflective surface 3A from normal incidence at partially reflective surface 3A, to an angle P away from normal, so that surface of interest 1 is intersected by rays 4A and 4B at a predetermined angle other than normal.

Illumination/detection subsystem 20 provides a source to illuminate surface of interest 1 through the resonator and a detection mechanism to detect changes in intensity of light leaving the resonator, whereby features of surface of interest 1 are measured. Focusing elements 5A, 5B as described above with respect to FIG. 4 are included to focus the light traveling along the resonant paths onto surface of interest 1 to improve the performance of the resonator by de-sensitizing the resonator to angular errors with respect to surface of interest 1

Figure 6A:
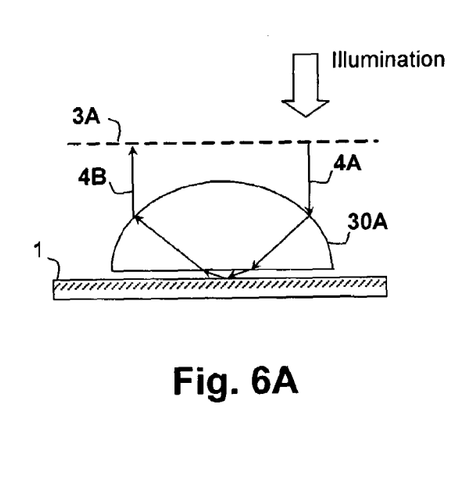
FIGS. 6A-6D are pictorial diagrams depicting dual-reflector optical resonators in accordance with embodiments of the invention.
Figure 6B:
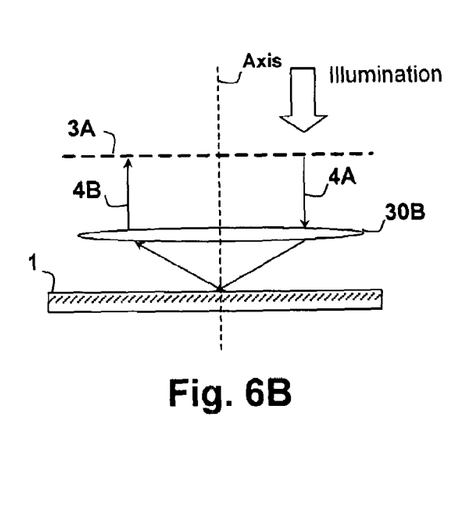

Referring now to FIGS. 6A-6D and particularly to FIG. 6A, elements for implementing the dual-reflector Fabry-Perot resonator of FIG. 5 are illustrated. FIG. 6A depicts a proximity lens that provides direction changing elements 12A, 12B together with focusing elements 5A-5B, in a single unit. Rays 4A, 4B are twice bent by the air-lens interfaces and strike surface of interest 1 at an angle close to grazing. FIG. 6B depicts a high numerical aperture (high NA) focusing system 30B positioned between surface of interest 1 that may be a lens, a combination of lenses or a mirror configuration that is illuminated off-axis, as shown, so that the angle of incident ray 4A is altered substantially before striking surface of interest 1. However, high-NA focusing system 30B is still operated in the imaging region, with an infinite conjugation ratio, so that resonance is supported between areas on partially reflective surface 3A and not individual points. Further, polarization effects in high-NA focusing system as with any of the direction changing elements of the present invention must be accounted for. Special coatings may be used to preserve polarization through focusing system 30B.

Figure 6C:
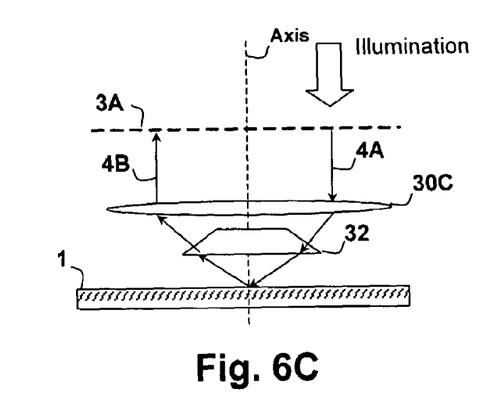
Figure 6D:
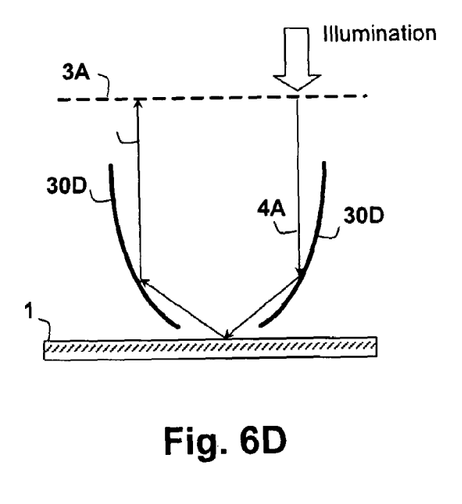

FIG. 6C depicts a Fabry-Perot resonator including a prism 32 for further increasing an incidence angle of ray 4A on surface of interest 1 that is positioned between focusing system 30C and surface of interest 1. FIG. 6D illustrates a Fabry-Perot resonator constructed with a parabolic mirror 30D used off-axis to provide the direction-changing and focusing elements, and will generally be constructed as a circularly symmetric shell having an aperture for passing light through to surface of interest 1, but could constitute two discrete parabolic mirrors.

Figure 7A:
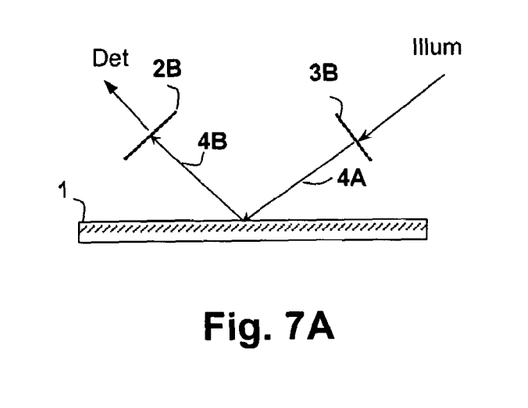
FIGS. 7A-7D are pictorial diagrams depicting triple-reflector optical resonators in accordance with embodiments of the invention.
Figure 7B:
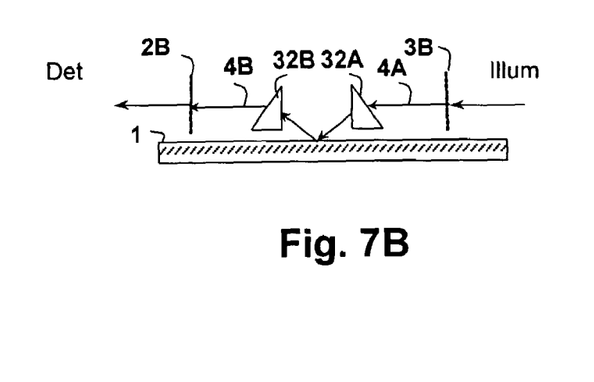

Referring now to FIGS. 7A-7D and particularly to FIG. 7A, elements for implementing the triple-reflector Fabry-Perot resonator of FIG. 4 are illustrated. FIG. 7A depicts a system having two partially reflective surfaces 3B and 2B at ends of a resonant path including incident ray 4A and reflected ray 4B, as described above. Detection is made at an end of the resonator opposing the illuminated end of resonator, also as described above. FIG. 7B illustrates a system including a pair of partially reflective surfaces 2B, 3B oriented in a direction perpendicular to surface of interest 1 and a pair of prisms 32A, 32B that are provided between partially reflective surfaces 2B, 3B the intersection of rays 4A, 4B, to alter the direction of the light incident on and reflected from surface of interest 1.

Figure 7C:
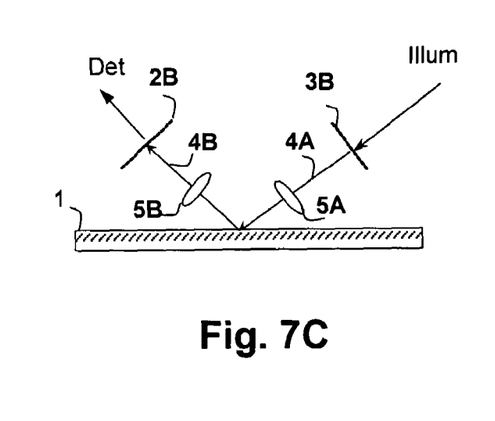
Figure 7D:
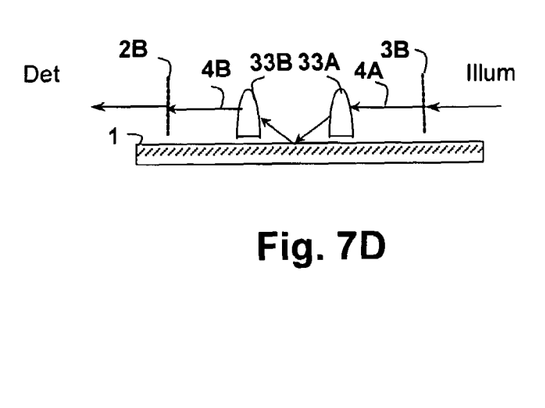

FIG. 7C illustrates incorporation of lenses 5A, 5B within the resonator, to increase spatial resolution and decrease sensitivity to the orientation of surface of interest 1. Finally, FIG. 7D illustrates a system for providing very near grazing incidence by using a pair of cut convex lenses 33A and 33B to alter the direction of and focus incident ray 4A onto surface of interest 1 and to collimate reflected ray 4B onto exit mirror 2B.

It should be understood for all of the above embodiments that the use of illustrative rays to indicate a resonant path illustrates only a single ray of an image. Incorporation of focusing elements may narrow the profile of the image at a particular surface, but multiple resonant paths exist in the above-described embodiments and the resonance is supported by multiple pairs of points on one or more partially or fully reflected surfaces, as long as the total path length around the resonator is resonant (i.e., an integral number of wavelengths) for that path.

Figure 8:
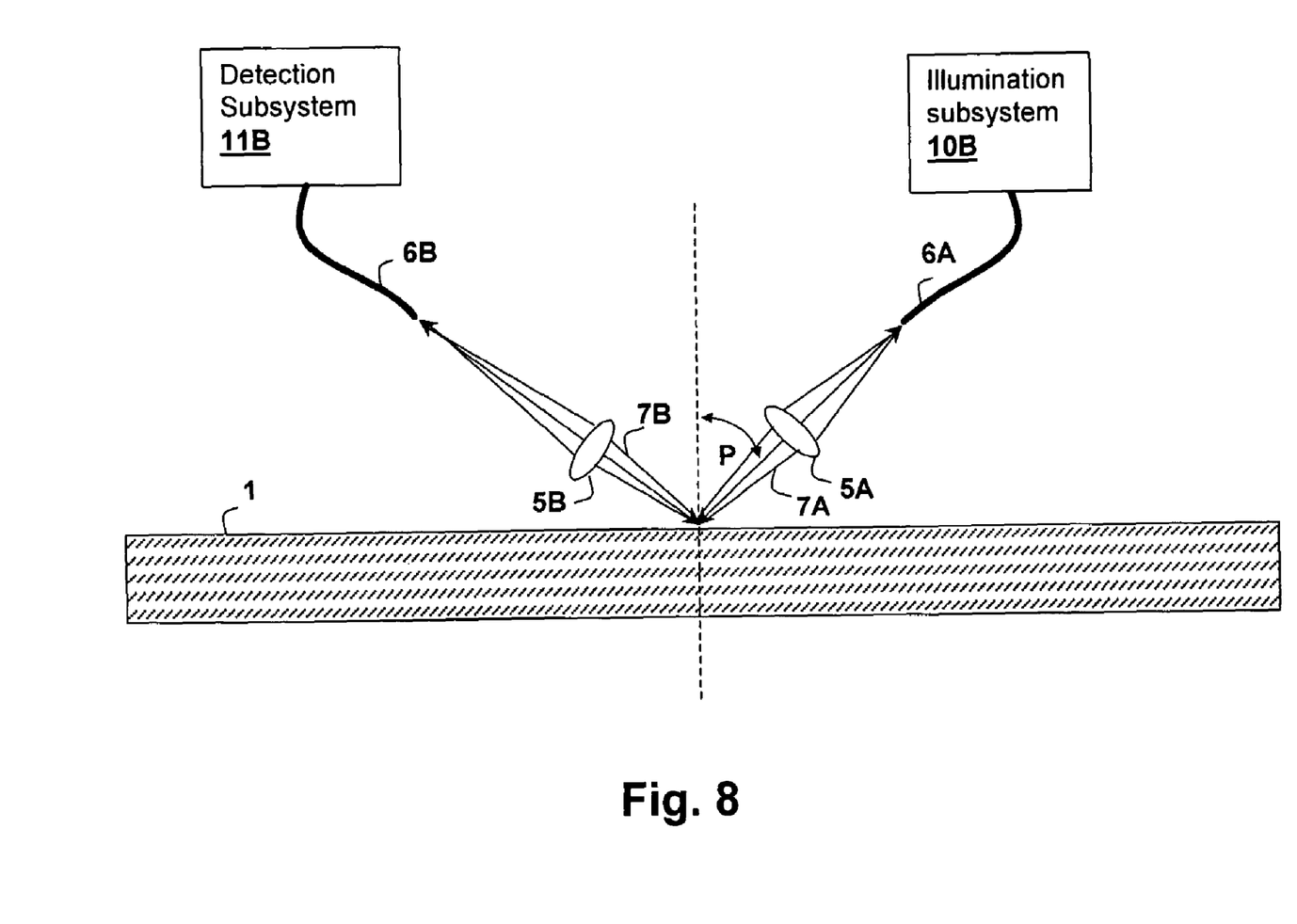
FIG. 8 is a pictorial diagram depicting a dual-reflector optical system in accordance with yet another embodiment of the invention.

Referring now to FIG. 8, an optical system in accordance with another embodiment of the present invention is depicted. The system of FIG. 8 is illustrative of a system in which a point illumination source and a point detector are imaged onto surface of interest 1 by a pair of imaging lenses 5A and 5B (finite conjugation ratio) focused on surface of interest at an angle of incidence other than normal. The point source and point detectors can be provided, as shown, by a pair of optical fibers 6A, 6B that couple their respective subsystem (illumination subsystem 10B and detection subsystem 11B) directly to the resonator. Optical fibers 6A, 6B have distal ends polished and coated with a partially reflective coating, so that the Fabry-Perot resonator is formed between the faces at the distal ends of optical fibers 6A, 6B. Imaging beams 7A and 7B intersect at a point on surface of interest 1 for which the length is resonant. Any misalignment of the focal axes of imaging lenses 5A and 5B, results only in a shift of the point of intersection of beams 7A and 7B to a point where the resonance is supported.

While the point source/point detector embodiment has disadvantages in that the mirror (fiber end) quality must be very high, the use of such a system is very advantageous in that no collimator is required to produce a small spot size and no separate mirrors are required to form the Fabry-Perot resonator, thus reducing the number of positioning variables in the system. The reduction in complexity and weight is also advantageous for scanning and data storage/retrieval device applications.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An optical resonator comprising:
    an illumination system;
    at least one reflector including at least one partially reflective surface for sustaining multiple internal reflections in a resonant cavity formed at least partially between said at least one reflector and a surface of interest, wherein light leaves said at least one reflector on an optical path normal to said at least one reflector, intersects said surface of interest at a predetermined non-zero angle from normal at said surface of interest and returns to said at least one reflector in a normal direction; and
    a detection system for detecting an intensity of light leaving said at least one partially reflective surface for determining variations in features of said surface of interest.

2. The optical resonator of claim 1, wherein said at least one reflector includes two partially reflective surfaces.

3. The optical resonator of claim 1, wherein said at least one reflector comprises:
    a first reflector positioned along a first optical path between said illumination system and said surface of interest; and
    a second reflector positioned on a side opposite said first reflector with respect to an intersection of said first optical path with said surface of interest and in a second optical path between said surface of interest and said second reflector, and wherein primary planes of said first reflector and said second reflector are oriented at angles having a magnitude of said predetermined angle with respect to said surface of interest.

4. The optical resonator of claim 3, further comprising:
    at least one first lens positioned between said first reflector and said surface of interest for focusing light between said first reflector and said surface of interest; and
    at least one second lens positioned between second reflector and said surface of interest for collimating light between said surface of interest and said second reflector.

5. The optical resonator of claim 4, wherein said at least one first lens and said at least one second lens each have a finite conjugation ratio for imaging a point of said surface of interest to corresponding points on said first reflector and said second reflector, respectively.

6. The optical resonator of claim 4, wherein said first optical path and said second optical path extend along primarily parallel paths to said surface of interest, wherein said first and second lenses have optical axes that are also parallel to the surface of interest but are positioned offset with respect to said first and second optical path, whereby said first lens focuses light traveling from said first reflector to said surface of interest at said predetermined non-zero angle, and wherein said second lens collimates light reflected from said surface of interest onto said second reflector.

7. The optical resonator of claim 3, further comprising:
a first direction-changing element positioned between said first reflector and said surface of interest for changing a direction of said first optical path from normal to said first reflector to said predetermined non-zero angle; and
a second direction-changing element positioned between said second reflector and said surface of interest for changing a direction of light leaving said surface of interest to a direction normal to said second reflector.

8. The optical resonator of claim 1, wherein said first reflector is a polished and coated partially-reflective end of a first optical fiber extending from said illumination system, and wherein said second reflector is a polished and coated partially reflective end of a second optical fiber extending to said detection system.

9. The optical resonator of claim 1, further comprising an optical focusing system positioned along said optical path between said first reflector and said intersection between said surface of interest and said optical path, wherein said optical focusing system alters an angle of incidence of said light from said optical path normal to said at least one reflector to a direction aligned along said predetermined non-zero angle with respect to said surface of interest.

10. The optical resonator of claim 9, wherein said optical focusing system is further positioned along a reflection optical path extending between said surface of interest and said optical path, wherein said optical focusing system further changes an angular direction of light leaving said surface of interest to a direction normal to said at least one reflector.

11. The optical resonator of claim 10, wherein said optical focusing system comprises a single lens positioned between said surface of interest and said at least one reflector, and wherein a return optical path of light leaving said surface of interest differs from an incident optical path of light incident upon said surface of interest.

12. The optical resonator of claim 9, wherein said optical focusing system is a high numerical aperture focusing system, and wherein said return optical path and said incident optical path pass though said high numerical aperture focusing system at positions substantially removed from the central axis of said high numerical aperture focusing system.

13. The optical resonator of claim 12, further comprising a prism positioned between said high numerical aperture focusing system and said surface of interest, wherein said prism is located within said incident optical path and said return optical path to further increase said predetermined angle.

14. The optical resonator of claim 9, wherein said optical focusing system is a proximity lens having a planar surface in proximity to said surface of interest and an opposing curved surface facing said at least one reflector.

15. The optical resonator of claim 9, wherein said optical focusing system comprises at least one parabolic mirror for altering said angle of incidence of said light.

16. The optical resonator of claim 15, wherein said optical focusing system comprises:
a first parabolic mirror positioned in said optical path between said at least one reflector and said surface of interest said angle of incidence of said light incident on said surface of interest to said predetermined non-zero angle from normal incidence; and
a second parabolic mirror positioned along a reflection optical path between said surface of interest and said at least one reflector for altering an angular direction of light leaving said surface of interest to a direction normal to said at least one reflector.

17. A method for improving performance of a resonator enhanced optical system, said method comprising:
repeatedly reflecting incident light in a cavity formed at least partially between at least one reflector including at least one partially reflective surface and a surface of interest, so that said light leaves said at least one reflector at a normal angle and intersects said surface of interest at a predetermined non-zero angle other than normal and returns to said at least one reflector in a normal direction; and
determining characteristics of said reflected light to detect features of said surface of interest.

18. The method of claim 17, further comprising partially transmitting light through said partially reflective surface whereby said determining is performed in conformity with said transmitted light.

19. The method of claim 17, wherein said at least one reflector surface is two reflectors, a first reflector positioned on an incident optical path between an illumination source and said surface of interest, and a second reflector positioned on an opposite aide of said surface of interest along a reflected optical path between said surface of interest and said second reflector, and wherein said repeatedly reflecting is performed between said first reflector and said second reflector.

20. The method of claim 19, further comprising:
focusing light traveling along said incident optical path; and
collimating light traveling along said reflected optical path.

21. The method of claim 20, wherein said focusing and collimating are performed with a finite conjugation ratio such that said focusing focuses light at a point of said surface of interest from a point on said at least one reflector and said collimating collimates light from said point of said surface of interest to a second point of said at least one reflector.

22. An optical resonator comprising:
an illumination system;
at least one reflector including at least one partially reflective surface for sustaining multiple internal reflections in a cavity formed at least partially between said at least one reflector and a surface of interest; and
means for directing light leaving said at least one reflector on an optical path normal to said at least one reflector to intersect said surface of interest at a predetermined non-zero angle from normal at said surface of interest and means for returning reflected light from said surface of interest to strike said at least one reflector in a normal direction.

* * * * *